United States Patent [19]

Stout

[11] Patent Number: 4,521,511

[45] Date of Patent: Jun. 4, 1985

[54] CATALYZED COLORIMETRIC AND FLUOROMETRIC SUBSTRATES FOR PEROXIDASE ENZYME DETERMINATIONS

[75] Inventor: Robert L. Stout, Overland Park, Kans.

[73] Assignee: Enzyme Technology Company, Overland Park, Kans.

[21] Appl. No.: 421,263

[22] Filed: Sep. 22, 1982

[51] Int. Cl.³ .................. C12Q 1/28; G01N 33/52; G01N 33/54
[52] U.S. Cl. .................................... 435/28; 435/805; 436/135; 436/826; 436/904
[58] Field of Search ............... 435/4, 7, 28, 805, 810; 436/826, 904, 66, 135

[56] References Cited

U.S. PATENT DOCUMENTS

| Re. 29,498 | 12/1977 | Meiattini | 435/28 |
|---|---|---|---|
| 3,668,076 | 6/1972 | Rey et al. | 436/66 |
| 4,251,222 | 2/1981 | White | 436/904 |
| 4,278,439 | 7/1981 | White | 436/904 |
| 4,340,392 | 7/1982 | Magers et al. | 435/28 |
| 4,340,393 | 7/1982 | Magers et al. | 435/28 |
| 4,340,394 | 7/1982 | Magers et al. | 435/28 |
| 4,418,037 | 11/1983 | Katsuyama et al. | 436/135 |

FOREIGN PATENT DOCUMENTS

| 0029926 | 6/1981 | European Pat. Off. | 435/28 |
|---|---|---|---|
| 1896 | 1/1981 | Japan | 435/28 |
| 54358 | 5/1982 | Japan | 435/28 |

OTHER PUBLICATIONS

Ralston et al., Canadian Journal of Biochemistry 1980, vol. 58, pp. 1270–1276.
Lyttle et al., Canadian Journal of Biochemistry 1973, vol. 51, pp. 1066–1071.
Pommier et al., The Journal of Biological Chemistry, vol. 254, No. 8, 1979, pp. 3006–3010.
Yeh et al., Canadian Journal of Biochemistry, vol. 49, 1971, pp. 163–165.

*Primary Examiner*—Robert J. Warden
*Assistant Examiner*—William J. Herald
*Attorney, Agent, or Firm*—Schmidt, Johnson, Hovey & Williams

[57] ABSTRACT

Improved catalyzed substrates for use in developing characteristic colors or fluorescence in the presence of peroxidase enzymes (e.g., horseradish peroxidase) are disclosed which include as a rate accelerator a substituted phenol such as a p-halogenated phenol. The complete system typically includes a peroxide type oxidizing agent (e.g., hydrogen peroxide), a chromogenic or flurogenic compound (e.g., ABTS), a buffer and the accelerator compound. Advantageously, the accelerator should provide at least about 50 percent rate enhancement for the substrate, as compared with an otherwise identical, accelerator-free substrate reacted under the same conditions; however, the most preferred accelerator, p-iodophenol, gives enhancements on the order to 1,000 percent. The invention is particularly useful in so-called ELISA determinations which involve an enzyme-linked moiety, and permit detection at very low concentration levels unobtainable with conventional colorimetric substrates.

5 Claims, 2 Drawing Figures

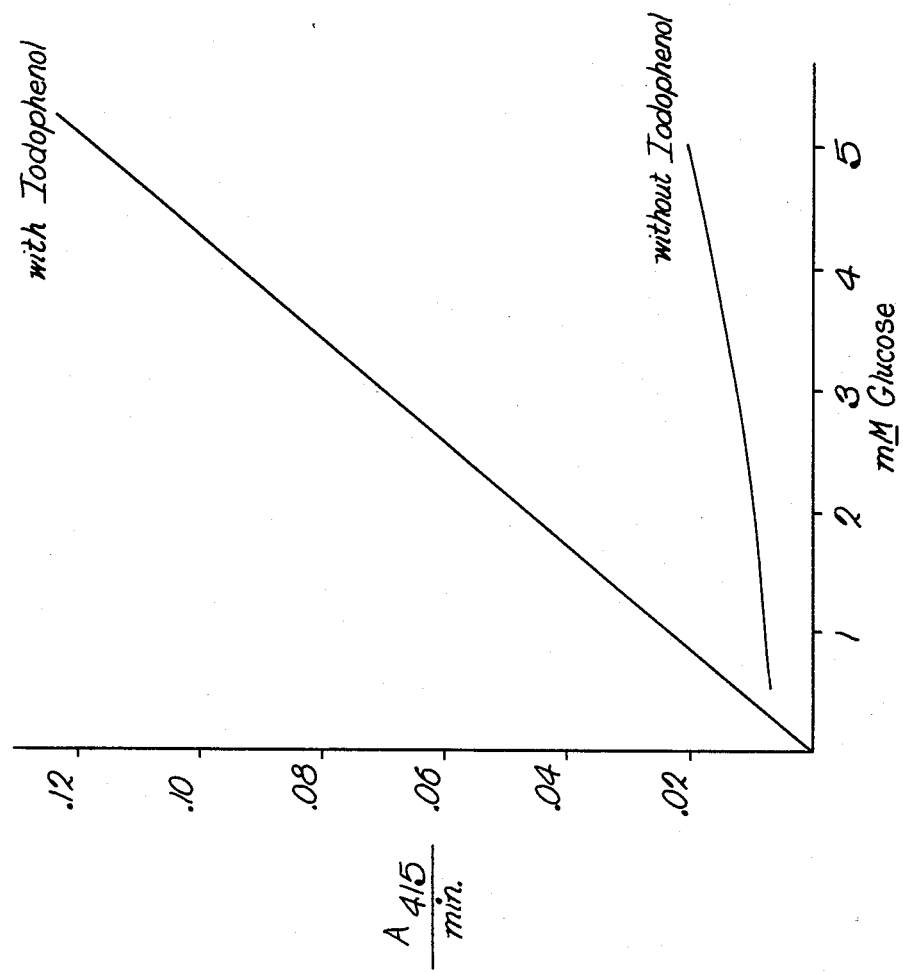
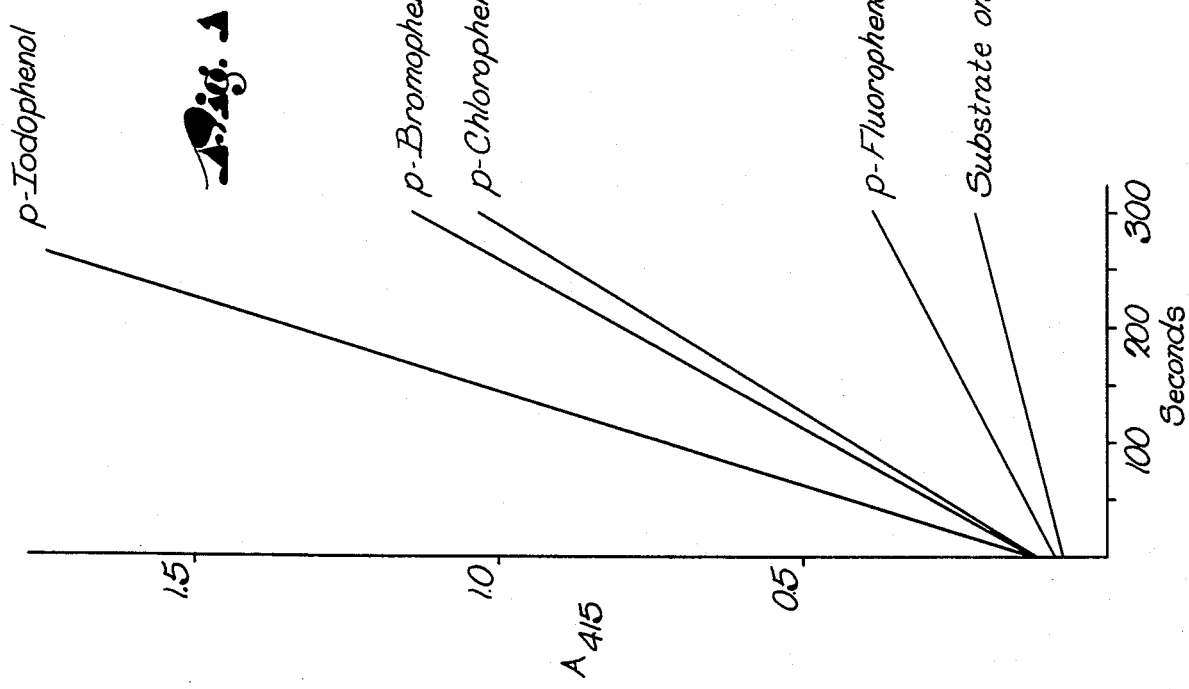

CATALYZED COLORIMETRIC AND FLUOROMETRIC SUBSTRATES FOR PEROXIDASE ENZYME DETERMINATIONS

BACKGROUND OF THE INVENTION

1. Field of the Invention

The present invention is concerned with improved colorimetric or fluorometric systems useful for developing characteristic colors or fluorescence in the presence of a peroxidase enzyme, or a peroxidase enzyme-linked moiety. More particularly, it is concerned with such systems and methods of use thereof, which utilize in the substrate an accelerator for enhancing the colorimetric or fluorometric reaction(s). Broadly speaking, the accelerator should be selected from the group consisting of substituted phenol compounds, and should provide significant rate enhancement when compared to identical, accelerator-free substrates.

2. Description of the Prior Art

The peroxidase enzymes, and particularly horseradish peroxidase, have become the enzymes of choice in many enzyme-linked immunoassay systems. Horseradish peroxidase is extremely stable, has high substrate turnover rate, and is able to yield both chromogenic and fluorogenic products from a variety of different substrates. The chromogenic substrates have proven to be ideal for visual qualitative determinations, while both types of substrates have found diverse applications in instrument monitored quantitative determinations. See *Worthington Enzymes*, Worthington Biochemical Corp., Freehold, N. J.; K. G. Paul (1963), *The Enzymes*, Vol. 9, Part B, Chapter 7, Academic Press, New York; and H. S. Mason, *Advances In Enzymol*, (1957) 19, 79.

Although perhaps the most widespread use of horseradish peroxidase is in conjunction with ELISA (enzyme linked immunoassay) determinations, its use has not been so limited. In fact, horseradish peroxidase can also be used in coupled assays for the detection and determination of glucose, galactose and certain amino acids in conjunction with their respective oxidases.

In those systems where a peroxidase enzyme is employed as a tag or label, the final determination, be it either qualitative or quantitative, is made either colorimetrically or fluorometrically. Typically, this involves reacting the enzyme with a colorimetric or fluorometric substrate which would normally include a peroxide type oxidizing agent, a compound capable of reacting and giving off color or fluorescence in the presence of the enzyme and the oxidizing agent, and a buffering system.

The net reaction of horseradish peroxidase (HRPO) in the presence of a normal substrate including a chromogenic or fluorometric compound ($AH_2$) may be represented schematically by:

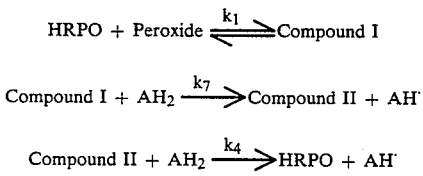

$$\text{HRPO} + \text{Peroxide} \underset{}{\overset{k_1}{\rightleftharpoons}} \text{Compound I} \qquad 1.$$

$$\text{Compound I} + AH_2 \xrightarrow{k_7} \text{Compound II} + AH\cdot \qquad 2.$$

$$\text{Compound II} + AH_2 \xrightarrow{k_4} \text{HRPO} + AH\cdot \qquad 3.$$

The primary products are radicals which react in solution and may form chromogenic or fluorogenic final products. Normally $k_7$ is much greater than $k_4$ and therefore the second electron abstraction is rate limiting. (B. Chance, Arch. Biochem. Biophy (1952), 41, 404, ibid. p. 416). Both reaction 2 and 3 above involve the transfer of a single electron from the substrate to the enzyme. (P. George, Nature (1952), 169, 612; B. Chance, Arch. Biochem. Biophy (1952), 41, 404, ibid. p. 416). $k_1$ is rate limiting only when hydrogen peroxide is present in limiting amount, and therefore any compound affecting the apparent rate probably affects $k_4$, i.e., the second electron abstraction. In any system employing a substrate of the type described above, any factor or catalyst that would accelerate the rate of product formation would effectively permit shorter assay times and increased sensitivity. That is to say, in an enzyme-linked immunoassay, the doubling of the rate would allow for interpretation of results in half the previous incubation time. A logical extension of this argument is that if time is held constant, then the test system should be able to detect half the amount of analyte previously detectable. Similar considerations apply to the coupled reactions utilizing unlinked horseradish peroxidase.

A number of assay conditions have been previously described which can cause such a desirable increase in enzyme activity. Compounds known to increase horseradish peroxidase activity include nitrogenous ligands (I. Fridovich, J. Biol. Chem. (1963), 238, 3921), palmitic acid (A. K. Mattoo and V. V. Modi (1975) Biochemica Biophys Acta 397, 381), and non-ionic detergents (B. Porstmann, et al. (1981) Clinica Chem Acta, 109, 175). In 1963, Fridovich demonstrated that the nitrogenous ligands ammonia, pyridine and imidazole increase the rate of peroxidation of dianisidine by horseradish peroxidase. In subsequent studies, Claiborne and Fridovich have suggested that the mechanism for this acceleration involves the nucleophilic base facilitating the abstraction of a second electron from the substrate radical intermediate. (Biochem (1979), 18, 2329). These authors also suggested that the 2 electron abstractions, as 2 distinct steps, is the true mechanism that occurs in the peroxidase reaction. If this proposed mechanism is correct the free-radical is bound to the enzyme and only released after a second electron is abstracted with the intermediate rearranging to form the product. However, this proposed divalent abstraction is at variance with other univalent and simple divalent proposals (B. Chance 1952, P. George, 1952, R. Roman and H. B. Dunford, Biochem (1972) 11, 2076, R. Roman and H. B. Dunford, Can. J. Chem. (1973) 51, 588). But the mechanism proposed by Claiborne & Fridovich, see the single electron abstraction described above (P. George, 1952, B. Chance, 1952), should be evaluated with caution for it is based on data collected with horseradish peroxidase catalyzed peroxidation of o-dianisidine and p-phenylenediamine two compounds known to participate in reversible two-electron oxidations (Piette et al., Ana. Chem. (1962), 34, 916). Fridovich (1963) also reported that peroxidation kinetics observed with o-dianisidine and p-phenylenediamine were not found with other horseradish peroxidase substrates. This may suggest that double electron abstraction occurs only where the substrate can easily undergo a double oxidation.

In addition to nitrogenous ligands, palmitic acid has been demonstrated to increase the rate of horseradish peroxidase peroxidation of o-dianisidine (Mattoo and Modi, 1975). But activation by palmitic acid occurs only at low substrate concentrations and may have no significant effect in analytical systems, such as enzyme-linked immunoassays, where substrate is present in great excess. However, the palmitic acid dependent activation may be of utility in oxidase coupled reactions where substrate depletion does occur. By comparison, while, palmitic acid activation of horseradish peroxidase appears to be of limited usefulness, the activation of horseradish peroxidase by non-ionic detergents has greater applicability.

The commercially available non-ionic detergents Tween 20 and Triton X-100 were demonstrated to increase the peroxidation of a number of different substrates by Porstmann, et al. (1981). In this system the analytical sensitivity in an enzyme-immunoassay was approximately doubled by the addition of non-ionic detergent. The non-ionic detergent dependent increase in activity is the result of decreased inactivation of horseradish peroxidase. The time and temperature dependent inactivation is possibly the result of formation of a terminal complex between hydrogen peroxide and enzyme, (H. Gallati, J. Clin. Chem. Clin. Biochem. (1977), 15, 699). This clearly illustrates a point noted above, i.e., by increasing the rate, Fridovich (1963), with ammonium ligands or maintenance of a rate, Porstmann, et al. (1981) with Tween 20, an increased analytical sensitivity is possible.

SUMMARY OF THE INVENTION

The present invention is at least in part based upon the discovery that certain substituted phenol compounds have the ability to greatly accelerate the chromogenic or fluorogenic reactions of substrates, and particularly those useful for developing colors or florescence in the presence of a peroxidase enzyme such as horseradish peroxidase. Broadly speaking, a system according to the invention would include a peroxide oxidizing agent, a compound capable of reacting and giving off color or florescence in the presence of peroxidase enzyme and the oxidizing agent, and an accelerator in accordance with the invention admixed with the system. The accelerator is taken from the group consisting of substituted phenol compounds, and should provide at least about 50 percent acceleration as compared with an otherwise identical substrate free of the accelerator and reacted under identical conditions.

Although a wide variety of accelerators are useful in the invention, the most preferred accelerators are selected from the group consisting of vanillin, 4-chloro-3-methylphenol and 4-iodophenol. Although the amount of accelerator used in a particular case is dependent upon a number of variables, including the type of chromogenic or fluorogenic compound used, in general the level of usage of the accelerators will vary from about 1 microgram up to about 1 milligram. Of course, the final usage level may be subject to adjustment through routine experimentation, but generally speaking the foregoing range will cover the vast majority of substrates and determinations in accordance with the invention.

Although the most preferred chromogenic or fluorogenic compound for use in the substrates of the invention is ABTS, i.e., 2,2'-azino-di-(3-ethyl-benzthiazolone-6-sulfonic acid), other such compounds are also useful. For example, phenol red, o-phenylenediamine, pyrogallol, 4-aminoantipyrine and bromopyrogallol red find utility in the invention.

BRIEF DESCRIPTION OF THE DRAWING

FIG. 1 is a graphical representation depicting the change in absorbence as a function of time for a series of accelerated substrates of the invention, and a non-accelerated conventional substrate; and FIG. 2 is a graph illustrating the absorbence readings for a series of glucose-containing samples using, respectively, an accelerated colorimetric substrate in accordance with the invention, and a conventional, non-accelerated colorimetric substrate.

DESCRIPTION OF THE PREFERRED EMBODIMENTS

As noted, the systems of the present invention are useful for developing a characteristic color or fluorescence in the presence of a peroxidase enzyme or a peroxidase enzyme-linked moiety. The systems of the invention generally include a peroxide oxidizing agent (most preferably hydrogen peroxide), a compound capable of reacting and giving off color or fluorescence in the presence of peroxidase enzyme and the peroxide oxidizing agent (e.g., ABTS), and an accelerator admixed with the substrate materials. The accelerator is advantageously taken from the group consistin of substituted phenol compounds, and should provide at least about 50 percent acceleration as compared with an otherwise identical system free of the accelerator and reacted under identical conditions.

Relative acceleration rates for colorimetric system are most advantageously determined spectrophotometrically. That is to say, a comparative test is run between a conventional system and the same system having admixed therein a substituted phenol accelerator in accordance with the invention. The tests are in all respects identical, save for the presence of the accelerator compound in one case, and involve reaction of the test system by adding thereto a minor amount of horseradish peroxidase. Spectrophotometric absorbance at a given wavelength (e.g., 415 nanometers) are then recorded as a function of time for each test system. The absorbance readings at the end of an identical time period are then compared for the conventional system and the accelerated system in accordance with the invention, by dividing the former into the latter and multiplying by 100. For practical purposes, at least about 50 percent increase in absorbance should be recorded for the accelerated system, as compared with the conventional control.

It has been found that the accelerators of the invention should preferably be taken from the group consisting of vanillin and compounds of the formula

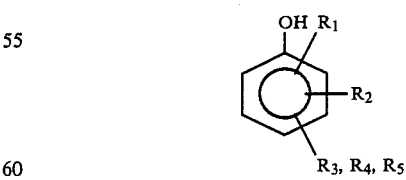

wherein $R_1$ is a halogen, a halogen-substituted phenoxy compound, a hydroxyphenone or a carboxylic acid or alkyl ester thereof; $R_2$ is hydrogen, hydroxy, a halogen, substituted and unsubstituted alkyl groups having from 1-6 carbon atoms, inclusive, an amino group, or a carboxylic acid or alkyl ester thereof; and $R_3$, $R_4$ and $R_5$ are respectively a halogen or hydrogen. In the above formula, the lead lines from the "R" substituents are indicative of the fact that the respective constituents can be located at any position about the phenol ring.

More preferred compounds in accordance with the invention are set forth in the following table, which also lists the respective acceleration rates achieved as compared with an otherwise identical, accelerator-free ABTS/$H_2O_2$/ buffer substrate.

TABLE I

| Accelerator | Approximate % Increase in Rate[1] |
|---|---|
| 2,5-dichlorophenol | 45 |
| 2,6-difluoroaniline | 45 |
| 3',3,5 triiodo-L-thyronine | 50 |
| m-bromophenol | 60 |
| o-chlorophenol | 60 |
| 4,4' dihydroxy-benzophenone | 66 |
| 4-fluorophenol | 86 |
| 3,5 diiodo-D-thyronine | 86 |
| 2,3 dichlorophenol | 90 |
| 4-chloro-2-methylphenol | 137 |
| 3,4-dichlorophenol | 184 |
| 3-iodo-L-tyrosine | 279 |
| 2,4-dibromophenol | 440 |
| p-chlorophenol | 520 |
| p-bromophenol | 570 |
| 2,4-dichlorophenol | 650 |
| vanillin | 900 |
| 4-chloro-3-methylphenol | 1000 |
| 4-iodophenol | 1000 |

[1]The above accelerators were tested with 0.8 mM 2,2'azino'di-(3-ethyl-benzthazolone-6-sulfonic acid) in 0.1M acetate, phosphate buffer (pH reaction was started by addition of 0.1 μg of horseradish peroxidase. Absorbance was recorded at 415 nanometers. The amount of increase was determined by:

$$\frac{A415 \text{ with accelerator}}{A415 \text{ without accelerator}} \times 100 = \% \text{ increase}$$

The following Examples illustrate the substrates and methods in accordance with the invention. It should be understood, however, that the Examples are for illustrative purposes only and should not be viewed as a limitation upon the overall scope of the invention.

EXAMPLE 1

A series of system solutions each containing 0.4 mg./ml. of 2,2'-azino-di-(3-ethyl-benzthiazolone-6-sulfonic acid) in 0.1 M sodium acetate, 0.1 M sodium phosphate (pH 6) containing 1.7 mM hydrogen peroxide were prepared. 0.05 mg./ml. of a p-halogenated phenol accelerator (either p-iodo,-bromo,-chloro or -flouro was added to each system except for an accelerator-free comparative control system. The respective system were tested by addition thereto of 0.1 micrograms of horseradish peroxidase, and the absorbance at 415 nanometers was recorded as a function of time. The results of this test are graphically depicted in FIG. 1, where it will be seen that the p-halogenated phenols all substantially accelerated the colorimetric reaction.

Similar rate enhancements have been observed with other system including those comprising phenol red, o-phenylenediamine, pyrogallol, 4-aminoantipyrine and bromopyrogallol red.

EXAMPLE 2

This example illustrates the use of p-iodophenol as an accelerator in an enzyme-linked immunoassay, and demonstrates that the accelerator permits detection at substantially lower concentrations as compared with the control.

Goat anti-human chorionic gonadotropin (hcG) was covalently coupled to latex beads with a water solube carbodiimide in phosphate buffer saline. A standard containing 500.m IU/ml. of hcG was prepared in hcG negative human urine. Four test tubes were prepared, and one hundred microliters of a 10% slurry of antibody coated beads was pipeted into each tube. One ml. of urine was then added to each tube, with two of the tubes being positive (with hcG) and two being negative (no hcG), followed by 200 ul. of horseradish peroxidase conjugated goat anti-hcG. The enzyme-antibody conjugation was via the sodium periodate method of Nakane, P. K. and A. Kawaoi (1974) J. Histochem. Cytochem 22, 1084. The tubes were then incubated at room temperature for 30 minutes, the beads then washed and the two sets of tests (one positive, one negative) were incubated with comparative colorimetric ABTS substrate system. One substrate contained 50 ug/ml. of p-iodophenol while the other substrate system contained no iodophenol but was otherwise identical. Following a 10 minute incubation with the respective system, the tubes were inspected visually and their absorbance determined at 415 nanometers in a Varian DMS-90 Spectrophotometer. The following table sets forth the test results:

TABLE II

| | No iodophenol | | With iodophenol | |
|---|---|---|---|---|
| | Positive | Negative | Positive | Negative |
| Visual reading | Colorless | Colorless | Colorless | Dark Green |
| $A_{415}$ reading | 0.05 | 0.06 | 0.09 | 0.98 |

These results clearly demonstrate that the accelerator allows for lower levels of detectability. With the accelerated substrate there is a substantial difference between positive and negative, while this is not the case in the accelerator-free controls.

EXAMPLE 3

This example describes a colorimetric system for the quantitative determination of the concentration of glucose in samples.

Two respective sets of standards for glucose concentration were prepared by the addition of, for each set, 0, 0.5, 1, 2, 3, 4, 5 millimolar glucose in water. A substrate solution containing 400 micrograms of 2,2'-azino-di-(3-ethyl-benzthiazolone-6-sulfonic acid), 10 micrograms of glucose oxidase, 0.1 microgram of horseradish peroxidase, 10 micrograms of p-iodophenol per milliliter in 0.1 M sodium acetate (pH 6.0) was prepared for each test sample in one set, whereas an iodophenol-free, otherwise identical substrate system was prepared for each test sample of the other set. The reactions were initiated by adding 10 microliters of the glucose samples respectively to 1 milliliter of each substrate solution, and the reactions were monitored at 415 nanometers with a Varian DMS-90 spectrophotometer. It is known that the horseradish peroxidase is an enzyme couple for the detection of hydrogen peroxide, the latter being a reaction product of glucose oxidase and glucose; hence, the result of the reactions will vary depending upon glucose concentration.

The results are graphically represented in FIG. 2. As illustrated, the values for the standards run without p-iodophenol are substantially lower than those run with iodophenol. By comparison, the rates of system containing iodophenol are linear and easily read.

In order to provide a comparison of the current and a standard method of glucose determination, two unknowns of glucose (I and II) were prepared and assayed in the presence of the above-described. system containing iodophenol, and with a Beckman Glucose II Analyzer, Beckman Instruments, Fullerton, Calif. The relative concentrations of the two unknowns were determined spectrophotometrically at 415 nanometers and using the FIG. 2 graph, with apparent concentrations being from the lower scale. The values obtained from this determination, and those using the Beckman instrument, are presented in Table III.

TABLE III

|  | Glucose II Analyzer | Present Invention |
|---|---|---|
| Unknown I | 1.85 mM | 1.90 mM |
| Unknown II | 4.1 mM | 3.9 mM |

The results obtained by both methods are very close, within experimental error, and further demonstrate the usefulness of the accelerated substrate of the invention.

I claim:

1. In a system for developing a characteristic color in the presence of a peroxidase enzyme, said system including a peroxide oxidizing agent and 2,2'-azino-di(3-ethyl-benzthiazolone-6-sulfonic acid), the improvement which comprises a rate accelerator added to the system at a level of from about 1 microgram to about 1 milligram and said rate accelerator being selected from the group consisting of vanillin and compounds of the formula

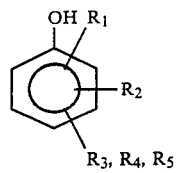

wherein $R_1$ is a halogen, a halogen-substituted phenoxy compound, a hydroxyphenone or a carboxylic acid or alkyl ester thereof; $R_2$ is hydrogen, hydroxy, a halogen, substituted and unsubstituted alkyl groups having from 1–6 carbon atoms, inclusive, an amino group, or a carboxylic acid or alkyl ester thereof; and $R_3$, $R_4$ and $R_5$ are respectively a halogen or hydrogen.

2. The system as set forth in claim 1, said accelerator being selected from the group consisting of 2,5-dichlorophenol, 2,6-difluroaniline, 3',3,5 triiodo-L-thyronine, m-bromophenol, o-chlorophenol, 4,4'-dihydroxy-benzophenone, 4-fluorophenol, 3,5 diiodo-D-thyronine, 2-3 dichlorophenol, 4-chloro-2-methylphenol, 3,4-dichlorophenol, 3-iodo-L-tyrosine, 2,4-dibromophenol, p-chlorophenol, p-bromophenol, 2,4-dichlorophenol, vanillin, 4-chloro-3-methylphenol and 4-iodophenol.

3. The system as set forth in claim 2, said accelerator being selected from the group consisting of vanillin, 4-chloro-3-methylphenol and 4-iodophenol.

4. The system as set forth in claim 1, said oxidizing agent being hydrogen peroxide.

5. The system as set forth in claim 1, including a buffer.

* * * * *